United States Patent [19]
Hillman et al.

[11] Patent Number: 6,057,108
[45] Date of Patent: May 2, 2000

[54] HUMAN ARF-RELATED PROTEINS

[75] Inventors: Jennifer L. Hillman; Olga Bandman, both of Mountain View; Karl J. Guegler, Menlo Park; Neil C. Corley, Mountain View; Henry Yue, Sunnyvale; Chandra Patterson, Mountain View, all of Calif.

[73] Assignee: Incyte Pharmaceuticals, Inc., Palo Alto, Calif.

[21] Appl. No.: 09/103,359

[22] Filed: Jun. 23, 1998

[51] Int. Cl.[7] .............................. C12Q 1/68; C12N 1/20; C12N 15/00; C12N 5/00; C07H 21/02
[52] U.S. Cl. .................... 435/6; 435/69.1; 435/252.3; 435/325; 435/320.1; 536/23.1
[58] Field of Search ........................... 435/6, 325, 252.1, 435/252.3, 69.1; 536/23.2, 23.1

[56] References Cited

PUBLICATIONS

Hillier et al., EMBL Database, Accession No. N31301, Jan. 1996.
Rothman, J.E. and Wieland, F.T., "Protein Sorting by Transport Vesicles," *Science*, 272:227–234 (1996).
Boman, A.L. and Kahn, R.A., "Arf proteins: the membrane traffic police," *Trends Biochem. Sci.*, 20:147–150 (1995).
Radhakrishna,H. And Donaldson, J.G., "ADP–Ribosylation Factor 6 Regulates a Novel Plasma Membrane Recycling Pathway," *The Journal of Cell Biology*, 139:49–61 (1997).
Tsuchiya, M., et al., "Molecular Identification of ADP–Ribosylation Factor mRNAs and Their Expression in Mammalian Cells," *The Journal of Biological Chemistry*, 266(5):2772–2777 (1991) (GI 178989).
Galas, M., et al., "Regulated Exocytosis in Chromaffin Cells," *The Journal of Biological Chemistry*, 272(5):2788–2793 (1997).
Suchy, S., et al., "Lowe Syndrome, a deficiency of a phosphatidyl–inositol 4,5–bisphosphate 5–phosphatase in the Golgi apparatus," *Human Molecular Genetics*, 4(12):2245–2250 (1995).
Marshansky, V., et al., "Receptor–mediated endocytosis in kidney proximal tubules: Recent advances and hypothesis," *Electrophoresis*, 18:2661–2676 (1997).
Lopez, I., et al., "Cloning and Initial Characterization of a Human Phospholipase D2 (hPLD2)," *The Journal of Biological Chemistry*, 273(21):12846–12852 (1998).
Tsuchiya, M., et al., (GI 178989 and GI 178988), GenBank Sequence Database (Accession No. M57763), National Center for Biotechnology Information, National Library of Medicine, Bethesda, Maryland 20894.

*Primary Examiner*—Ponnathapu Achutamurthy
*Assistant Examiner*—M. Monshipouri
*Attorney, Agent, or Firm*—Incyte Pharmaceuticals, Inc.

[57] ABSTRACT

The invention provides human ARF-related proteins (HARP) and polynucleotides which identify and encode HARP. The invention also provides expression vectors, host cells, antibodies, agonists, and antagonists. The invention also provides methods for diagnosing, treating, or preventing disorders associated with expression of HARP.

10 Claims, 8 Drawing Sheets

```
5' CT TTT TCA GGN GCT CGC TCN CAG CCA GAG ACG CTG CTT TTT TCC GGG
                                                                    53

TTC GGA GCC GTT CCG GAT GCT TTA GGC TGC CGG ATG TCT GAT CTC CGG ATA ACT
                                                       M   S   D   L   R   I   T
                                                                    107

GAG GCG TTT CTG TAC ATG GAT TAT CTG TGT TTT AGA GCA CTT TGC AAG GGA
    E   A   F   L   Y   M   D   Y   L   C   F   R   A   L   C   K   G
                                                                    161

CCA CCT GCA CCA CGA GAA TAT GAC CTG GTT TGC ATA GGC CTC ACA GGT TCT
    P   P   A   P   R   E   Y   D   L   V   C   I   G   L   T   G   S
                                                                    215

GGC AAA ACC AGT CTG TTG TCC AAA ATT TGC AGT GAA AGC CCC GAT AAC GTC GTG
    G   K   T   S   L   L   S   K   I   C   S   E   S   P   D   N   V   V
                                                                    269

TCG ACC ACA GGT TTT AGT ATT AAA GCA GTG CCA TTC CAG AAT GCC ATC TTG AAT
    S   T   T   G   F   S   I   K   A   V   P   F   Q   N   A   I   L   N
                                                                    323
```

FIGURE 1A

```
GTA AAA GAA CTT GGA GCT GAT AAC ATC CGG AAA TAC TGG AGC CGC TAC TAC
 V   K   E   L   G   A   D   N   I   R   K   Y   W   S   R   Y   Y
332         341         350         359         368         377

CAA GGA TCT CAA GGG GTA ATA TTT GTA TTA GAC AGT GCC TCT TCA GAG GAT GAT
 Q   G   S   Q   G   V   I   F   V   L   D   S   A   S   S   E   D   D
386         395         404         413         422         431

TTA GAA GCT GCT AGA AAT GAG CTG CAC TCA GCT CTT CAG CAT CAA CCA CAG TTA TGC
 L   E   A   A   R   N   E   L   H   S   A   L   Q   H   Q   P   Q   L   C
440         449         458         467         476         485

ACT TTA CCC TTT TTA ATA TTG GCC AAT CAT CAA GAC AAG CCA CTT GAA GCN CGC TCA
 T   L   P   F   L   I   L   A   N   H   Q   D   K   P   L   A   R   S
494         503         512         521         530         539

GTA CAA GAG ATN AAA TAT TTT GAA CTT GAA CCA CTT GCN CGT GGA AAA CGC
 V   Q   E   X   K   Y   F   E   L   E   P   L   A   R   G   K   R
548         557         566         575         584         593

TGG ATT CTA CAG CCC TGC TCA CTG GAT GAC CTG GAT GGC NCT GNA AGA CCA GNT
 W   I   L   Q   P   C   S   L   D   D   L   D   G   X   X   R   P   X
602         611         620         629         638         647
```

FIGURE 1B

```
       656       665       674       683       692       701
CTC TCA GNN GAN TNN NTT GTT AGA AAA AGA CCA TGA AGC TGT AAG NAT GGT
 L   S   X   X   X   X   V   R   K   R   P 710       719       728       737       746       755
GAA ATT CTG GGC AAA GAA AAC AGG GCT CCC CNA AAG GGC CTT GAA ACC TAT CAT 764       773       782       791       800       809
GTT AGT TTC CTC ATT TTA ATN TTA ATT TTG GGN AAT CCA GAC TAT ATT GGG GCT 818       827       836       845       854       863
TCC GGA ATC CAA NTT TTC CNC CTG GNG CAT TTT CCA GAC TTN TCC ATC TTC TCC 872       881       890       899       908       917
CAA TTT AAA NGG GAA TNA TTC CTG GTN GGA TTC CGG ATG GAA TTT ATC CTG NGG

NGC   3'
```

FIGURE 1C

```
5'    8           17          26          35          44          53
   TA AAC ACA TCT AGG TTC TTG TTC TTA GAA TAC AGC ATG AAG AAT TTG CTT TCT 62          71          80          89          98          107
   TCT TTC TTC CTA ACA TTT TCA TGT GAG ATC CAG AAA GGA CAC ATT GTC TCT GGC 116         125         134         143         152         161
   CAT TCG AAG AAA GAA AGA AAG AAA AAA GAA ATT TAG AGA CAG AGA GAG 170         179         188         197         206         215
   AAA GCT GAA ATG GGT TCG CTG GGT TCT AAA AAT CCG CAA ACC AAA CAA GCC
        A   E   M   G   S   L   G   S   K   N   P   Q   T   K   Q   A 224         233         242         251         260         269
   CAA GTT CTT CTT TTG GGA CTT GAC TCA GCT GGG AAG TCT ACT CTC TAT AAA
    Q   V   L   L   L   G   L   D   S   A   G   K   S   T   L   Y   K 278         287         296         305         314         323
   TTA AAG CTT GCT AAG GAT ATT ACC ACC ATC CCT ACA ATA GGT TTC AAT GTG GAA
    L   K   L   A   K   D   I   T   T   I   P   T   I   G   F   N   V   E 332         341         350         359         368         377
   ATG ATC GAG TTG GAA AGG AAT CTT TCA CTC ACA GAT GTC TGG GAT GTT GGA GGA CAG
    M   I   E   L   E   R   N   L   S   L   T   D   V   W   D   V   G   G   Q
```

FIGURE 2A

```
      386            395            404            413            422            431
GAA AAA ATG AGA ACT GTT TGG GGC TGT TAC TGT GAG AAC ACC GAT GGG CTG GTG
 E   K   M   R   T   V   W   G   C   Y   C   E   N   T   D   G   L   V 440            449            458            467            476            485
TAT GTT GAC AGT ACA GAC AAA CAG CGA CTG GAA GAG TCT CAG AGA CAG TTT
 Y   V   D   S   T   D   K   Q   R   L   E   E   S   Q   R   Q   F 494            503            512            521            530            539
GAG CAC ATT TTG AAG AAT GAA CAC ATT AAA AAT GTG CCT GTT CTA TTA GCC
 E   H   I   L   K   N   E   H   I   K   N   V   P   V   L   L   A 548            557            566            575            584            593
AAC AAA CAA GAC ATG CCT GGA GCT CTG ACT GCT GAG GAC ATC ACC AGA ATG TTC
 N   K   Q   D   M   P   G   A   L   T   A   E   D   I   T   R   M   F 602            611            620            629            638            647
AAA GTG AAG AAG CTT TGC AGT GAC CGG AAC TGG TAT GTG CAA CCC TGC TGT GCC
 K   V   K   K   L   C   S   D   R   N   W   Y   V   Q   P   C   C   A 656            665            674            683            692            701
CTC ACA GGG GAG GGG CTG GCC CAG GGG TTC AGG AAA TTA GGA TTT GTG AAG
 L   T   G   E   G   L   A   Q   G   F   R   K   L   G   F   V   K 710            719            728            737            746            755
AGC CAC ATG AAA TCA AGA GGA GAC ACT TTG GCG TTC TTC AAG CAG AAC TGA GGC
 S   H   M   K   S   R   G   D   T   L   A   F   F   K   Q   N
```

FIGURE 2B

```
       764         773         782         791         800         809
TGC GAA AAA TCC AAG TCT CTA CAG AGA CAC TGA AGT TGA AAG GGT ATT TGT 818         827         836         845         854         863
TTT TCC ATG CCC AAT GAG GAA ATC AAA TTA ATG AGT TGA CAA ACT TTT CCT GAG 872         881         890         899         908         917
ATG TAA TTT CAT CTA TTA GGT AAA ACA CCT AAG AAT GGT ATC CAA GAA AAT 926         935         944         953         962         971
AAT TTA ATT TTC AAG CAA GGG AAC TTT AGG CCA ACC TTG TGG CCA TTG ATC CAC 980         989         998
CGG GGA ATT GAA AAC GGT ATA ATG GTT CTC ACA T 3'
```

FIGURE 2C

```
1    MSDLRITEAFLYMDYLCFRALCCKGPPPAR    823143
1    MGKV-LSKIF------------------GN    GI 178989

31   PEYDLVCIGLTGSGKTSLLSKLCSESPDNV    823143
12   KEMRILMLGLDAAGKTTILYKLKLGQSVTT    GI 178989

61   VSTTGFSIKAVPFQNAILNVKELGGADNIR    823143
42   IPTVGFNVETVTYKNVKFNWDVGGQDKIR    GI 178989

91   KYWSRYYQGSQGVIFVLDSASSEDDLEAAR    823143
72   PLWRHYYTGTQGLIFVVDCADR-DRIDEAR    GI 178989

121  NELHSALQHPQLCTLPFLILANHQDKPAAR    823143
101  QELHRIINDREMRDAIILIFANKQDLPDAM    GI 178989

151  SVQEXKKYFELEPLXRGKRWILQPCSLDDL    823143
131  KPHEIQEKLGLTR-IRDRNWYVQPSCATSG    GI 178989

181  DGXXRPXLSXXXXVRRKRP              823143
160  DGLYE-GLTWLTS--NYKS              GI 178989
```

FIGURE 3

```
  1  MGSLGSKNPQTKQAQVLLLGLDSAGKSTLL   1333754
  1  MGKVLSKIFGNKEMRILMLGLDAAGKTTIL   GI 178989

31  YKLKLAKDITTIPTIGFNVEMIELERNLSL   1333754
 31  YKLKLGQSVTTIPTVGFNVETVTY-KNVKF   GI 178989

61  TVWDVGGQEKMRTVWGCYCENTDGLVYVVD   1333754
 60  NVWDVGGQDKIRPLWRHYYTGTQGLIFVVD   GI 178989

91  STDKQRLEESQRQFEHILKNEHIKNVPVVL   1333754
 90  CADRDRIDEARQELHRIINDREMRDAIILI   GI 178989

121  LANKQDMPGALTAEDITRMFKVKKLCSDRN   1333754
120  FANKQDLPDAMKPHEIQEKLGLTRI-RDRN   GI 178989

151  WYVQPCCALTGEGLAQGFRKLTGFVKSHMK   1333754
149  WYVQPSCATSGDGLYEGLTWLTSNYKS      GI 178989

181  SRGDTLAFFKQN                     1333754
175                                   GI 178989
```

FIGURE 4

HUMAN ARF-RELATED PROTEINS

FIELD OF THE INVENTION

This invention relates to nucleic acid and amino acid sequences of human ARF-related proteins and to the use of these sequences in the diagnosis, treatment, and prevention of secretory and epithelial disorders, including those disorders associated with inflammation.

BACKGROUND OF THE INVENTION

Cells traffic molecules to appropriate subcellular organelles and the extracellular environment by the process of vesicle fission from a donor compartment and fusion with an acceptor compartment. A paradigm for vesicle formation, translocation, docking, and fusion has been described and a number of molecules involved in the process have been identified. These include N-ethylmaleimide-sensitive fusion protein (NSF), soluble NSF attachment proteins (SNAP), and the vesicular- and target-specific SNAP receptors (v- and t-SNAREs, respectively). Many of the signaling pathways providing the cue for vesicle fusion have also been defined. For example, stimulation of chromaffin cells by a cholinergic agonist leads to exocytosis of stored secretory granules and release of catecholamines. Monomeric GTP-binding proteins have been shown to act as regulatory molecules, or "switches", for linking these two processes. The ADP-ribosylation factor (Arf) family of proteins is one such class of regulatory molecule. (Rothman, J. E. and Wieland, F. T. (1996) Science 272: 227–234.)

Arfs were originally identified as cofactors for the cholera toxin-dependent ADP ribosylation of the heterotrimeric G protein, $G_S$. Arfs were later characterized as monomeric GTP-binding proteins, related structurally to both G protein α-subunits and Ras proteins. The Arf family members share more than 60% sequence identity, appear to be ubiquitous in eukaryotes, and are highly conserved throughout evolution. For example, *Drosophila melanogaster, Shigosaccharomyces pombe,* and human ARF1 share more than 90% sequence identity. All Arf family members are myristoylated at the N-terminal glycine residue and associate with membranes in a GTP-dependent manner. Arfs also activate phospholipase D (PLD), a membrane-bound enzyme implicated as an effector of several growth factors. (Boman, A. L. and Kahn, R. A. (1995) Trends Biochem. Sci. 20: 147–150.)

Arf family members fall into three classes according to their size and sequence homology. ARF1, ARF2, and ARF3 form class I, ARF4 and ARF5 form class II, and ARF6 forms class III. These classes occupy different subcellular locations and have been implicated in different transport pathways. Class I Arfs localize to the Golgi where they are involved in the regulation of ER-Golgi and intra-Golgi transport. Class I Arfs are also involved in the recruitment of cytosolic coat proteins to Golgi membranes during the formation of transport vesicles. Class III ARF6 localizes to a tubulovesicular compartment, secretory granules, and the plasma membrane, where it is involved in regulated secretion and recycling. Class II Arfs appear to be cytosolic, but their role has not been elucidated. (Boman, supra; Radhakrishna, H. and Donaldson, J. G. (1997) J. Cell Biol. 139: 49–61; and Tsuchiya, M. (1991) J. Biol. Chem. 266: 2772–2777.)

Arf function is regulated by a GDP-GTP cycle. The role of Arf in vesicle formation has been best studied for ARF1. ARF1 is cytosolic in the GDP bound state, but is associated with membranes when in the GTP bound state. A guanine nucleotide exchange factor (GEF) in the donor compartment recruits ARF1 to the membrane. At the membrane, GTP-ARF1 recruits coat proteins, which assemble together into spherical coats, budding off vesicles in the process. After budding, hydrolysis of bound GTP causes ARF1 to dissociate from the membrane. ARF1 dissociation causes the coat to become unstable and dissociate as well. (Rothman, supra.)

The role of Arf in regulated secretion has been best studied for ARF6. ARF6 is localized to an intracellular compartment in its GDP bound state. This compartment is composed of secretory granules in chromaffin cells and a tubulovesicular compartment in transfected HeLa and CHO cells. ARF6 translocates to the plasma membrane in its GTP bound state and reorganizes the actin skeleton into protrusive plasma membrane extensions, reminiscent of exocytotic events. Analysis of mutants that lock ARF6 into its GDP (T27N) or GTP (Q67L) bound state has verified the nucleotide dependence of this localization pattern. (Radhakrishna, supra.) Studies have shown that this conversion and translocation of ARF6 is regulated by cell signaling pathways. For example, stimulation of chromaffin cells by cholinergic agonists caused ARF6 translocation, and this translocation was required for subsequent catecholamine release. (Galas, M-C. (1997) J. Biol. Chem. 272: 2788–2793.) Together these findings suggest a critical role for ARF6 in regulated secretory processes.

Arf family members have been implicated in several disease processes. Lowe's syndrome, an X-linked disorder characterized by congenital cataracts, renal tubular dysfunction and neurological deficits, may be due to an inability to recruit Arf to the Golgi membrane. (Suchy, S. F. et al. (1995) Hum. Mol. Genet. 4: 2245–2250). It has been suggested that regulation of Arf is also involved in cystic fibrosis, Dent's disease, diabetes and autosomal dominant polycystic kidney disease. (Marshansky, V., et al. (1997) Electrophoresis 18: 2661–2676.)

The discovery of new human ARF-related proteins and the polynucleotides encoding them satisfies a need in the art by providing new compositions which are useful in the diagnosis, treatment, and prevention of secretory and epithelial disorders, including those disorders associated with inflammation.

SUMMARY OF THE INVENTION

The invention features substantially purified polypeptides, human ARF-related proteins, referred to collectively as "HARP" and individually as "HARP-1" and "HARP-2." In one aspect, the invention provides a substantially purified polypeptide comprising an amino acid sequence selected from the group consisting of SEQ ID NO:1, SEQ ID NO:2, a fragment of SEQ ID NO:1, and a fragment of SEQ ID NO:2.

The invention further provides a substantially purified variant having at least 90% amino acid identity to the amino acid sequences of SEQ ID NO:1 or SEQ ID NO:2, or to a fragment of either of these sequences. The invention also provides an isolated and purified polynucleotide encoding the polypeptide comprising an amino acid sequence selected from the group consisting of SEQ ID NO:1, SEQ ID NO:2, a fragment of SEQ ID NO:1, and a fragment of SEQ ID NO:2. The invention also includes an isolated and purified polynucleotide variant having at least 90% polynucleotide sequence identity to the polynucleotide encoding the polypeptide comprising an amino acid sequence selected from the group consisting of SEQ ID NO:1, SEQ ID NO:2, a fragment of SEQ ID NO:1, and a fragment of SEQ ID NO:2.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:2, a fragment of SEQ ID NO:1, and a fragment of SEQ ID NO:2, as well as an isolated and purified polynucleotide having a sequence which is complementary to the polynucleotide encoding the polypeptide comprising the amino acid sequence selected from the group consisting of SEQ ID NO:1, SEQ ID NO:2, a fragment of SEQ ID NO:1, and a fragment of SEQ ID NO:2.

The invention also provides an isolated and purified polynucleotide comprising a polynucleotide sequence selected from the group consisting of SEQ ID NO:3, SEQ ID NO:4, a fragment of SEQ ID NO:3, and a fragment of SEQ ID NO:4. The invention further provides an isolated and purified polynucleotide variant having at least 90% polynucleotide sequence identity to the polynucleotide sequence comprising a polynucleotide sequence selected from the group consisting of SEQ ID NO:3, SEQ ID NO:4, a fragment of SEQ ID NO:3, and a fragment of SEQ ID NO:4, as well as an isolated and purified polynucleotide having a sequence which is complementary to the polynucleotide comprising a polynucleotide sequence selected from the group consisting of SEQ ID NO:3, SEQ ID NO:4, a fragment of SEQ ID NO:3, and a fragment of SEQ ID NO:4.

The invention further provides an expression vector containing at least a fragment of the polynucleotide encoding the polypeptide comprising an amino acid sequence selected from the group consisting of SEQ ID NO:1, SEQ ID NO:2, a fragment of SEQ ID NO:1, and a fragment of SEQ ID NO:2. In another aspect, the expression vector is contained within a host cell.

The invention also provides a method for producing a polypeptide comprising the amino acid sequence selected from the group consisting of SEQ ID NO:1, SEQ ID NO:2, a fragment of SEQ ID NO:1, and a fragment of SEQ ID NO:2, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:2, a fragment of SEQ ID NO:1, and a fragment of SEQ ID NO:2 in conjunction with a suitable pharmaceutical carrier.

The invention further includes a purified antibody which binds to a polypeptide comprising the amino acid sequence selected from the group consisting of SEQ ID NO:1, SEQ ID NO:2, a fragment of SEQ ID NO:1, and a fragment of SEQ ID NO:2, as well as a purified agonist and a purified antagonist to the polypeptide. The invention also provides a method for treating or preventing an epithelial disorder, the method comprising administering to a subject in need of such treatment an effective amount of a pharmaceutical composition comprising a substantially purified polypeptide having an amino acid sequence selected from the group consisting of SEQ ID NO:1, SEQ ID NO:2, a fragment of SEQ ID NO:1, and a fragment of SEQ ID NO:2.

The invention also provides a method for treating or preventing a secretory disorder, the method comprising administering to a subject in need of such treatment an effective amount of a pharmaceutical composition comprising a substantially purified polypeptide having an amino acid sequence selected from the group consisting of SEQ ID NO:1, SEQ ID NO:2, a fragment of SEQ ID NO:1, and a fragment of SEQ ID NO:2.

The invention also provides a method for detecting a polynucleotide encoding the polypeptide comprising the amino acid sequence selected from the group consisting of SEQ ID NO:1, SEQ ID NO:2, a fragment of SEQ ID NO:1, and a fragment of SEQ ID NO:2 in a biological sample containing nucleic acids, the method comprising the steps of: (a) hybridizing the complement of the polynucleotide sequence encoding the polypeptide comprising the amino acid sequence selected from the group consisting of SEQ ID NO:1, SEQ ID NO:2, a fragment of SEQ ID NO:1, and a fragment of SEQ ID NO:2 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the nucleic acids of the biological sample are amplified by the polymerase chain reaction prior to the hybridizing step.

BRIEF DESCRIPTION OF THE FIGURES

FIGS. 1A, 1B, and 1C show the amino acid sequence (SEQ ID NO:1) and nucleic acid sequence (SEQ ID NO:3) of HARP-1. The alignments were produced using MacDNASIS PRO™ software (Hitachi Software Engineering Co. Ltd., San Bruno, Calif.).

FIGS. 2A, 2B, and 2C show the amino acid sequence (SEQ ID NO:2) and nucleic acid sequence (SEQ ID NO:4) of HARP-2.

FIG. 3 shows the amino acid sequence alignment between HARP-1 (Incyte Clone number 823143; SEQ ID NO:1) and human ADP-ribosylation factor-6 (GI 178989; SEQ ID NO:14). The alignments were produced using the multisequence alignment program of LASERGENE™ software (DNASTAR Inc, Madison WI).

FIG. 4 shows the amino acid sequence alignment between HARP-2 (Incyte Clone number 1333754; SEQ ID NO:2) and human ADP-ribosylation factor-6 (GI 178989; SEQ ID NO:14).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HARP," as used herein, refers to the amino acid sequences of substantially purified HARP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HARP, increases or prolongs the duration of the effect of HARP. Agonists may include proteins, nucleic acids, carbohydrates, or any other molecules which bind to and modulate the effect of HARP.

An "allelic variant," as this term is used herein, is an alternative form of the gene encoding HARP. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding HARP, as described herein, include those sequences with deletions, insertions, or substitutions of different nucleotides, resulting in a polynucleotide the same as HARP or a polypeptide with at least one functional characteristic of HARP. Included within this definition are polymorphisms which may or may not be readily detectable using a particular oligonucleotide probe of the polynucleotide encoding HARP, and improper or unexpected hybridization to allelic variants, with a locus other than the normal chromosomal locus for the polynucleotide sequence encoding HARP. The encoded protein may also be "altered," and may contain deletions, insertions, or substitutions of amino acid residues which produce a silent change and result in a functionally equivalent HARP. Deliberate amino acid substitutions may be made on the basis of similarity in polarity, charge, solubility, hydrophobicity, hydrophilicity, and/or the amphipathic nature of the residues, as long as the biological or immunological activity of HARP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of HARP which are preferably at least 5 to about 15 amino acids in length, most preferably at least 14 amino acids, and which retain some biological activity or immunological activity of HARP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp. 1–5.)

The term "antagonist," as it is used herein, refers to a molecule which, when bound to HARP, decreases the amount or the duration of the effect of the biological or immunological activity of HARP. Antagonists may include proteins, nucleic acids, carbohydrates, antibodies, or any other molecules which decrease the effect of HARP.

As used herein, the term "antibody" refers to intact molecules as well as to fragments thereof, such as Fab, F(ab')$_2$, and Fv fragments, which are capable of binding the epitopic determinant. Antibodies that bind HARP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HARP, or of any oligopeptide thereof, to induce a specific immune response in appropriate animals or cells and to bind with specific antibodies.

The terms "complementary" or "complementarity," as used herein, refer to the natural binding of polynucleotides by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation or an aqueous solution. Compositions comprising polynucleotide sequences encoding HARP or fragments of HARP may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g.,sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HARP, by Northern analysis is indicative of the presence of nucleic acids encoding HARP in a sample, and thereby correlates with expression of the transcript from the polynucleotide encoding HARP.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison Wis.). The MegAlign™ program can create alignments between two or more sequences according to different methods, e.g., the clustal method. (See, e.g., Higgins, D. G. and P. M. Sharp (1988) Gene 73: 237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183: 626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15: 345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of HARP. For example, modulation may cause an increase or a decrease in protein activity, binding characteristics, or any other biological, functional, or immunological properties of HARP.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked," as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8: 53–63.)

The term "sample," as used herein, is used in its broadest sense. A biological sample suspected of containing nucleic acids encoding HARP, or fragments thereof, or HARP itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HARP polypeptides, as used herein, refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

The term "variant," when used in the context of a polynucleotide sequence, may encompass a polynucleotide sequence related to HARP. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

The Invention

The invention is based on the discovery of new human ARF-related proteins (HARP), the polynucleotides encoding HARP, and the use of these compositions for the diagnosis, treatment, or prevention of secretory and epithelial disorders, including those disorders associated with inflammation.

Nucleic acids encoding the HARP-1 of the present invention were first identified in Incyte Clone 823143 from the epidermal breast keratinocyte cDNA library (KERANOT02) using a computer search, e.g., BLAST, for amino acid sequence alignments. A consensus sequence, SEQ ID NO:3, was derived from the following overlapping and/or extended nucleic acid sequences: Incyte Clones 3464110H1 (293TF2T01), 3384609H1 (ESOGNOT04), and 823143R6 and 823143H1 (KERANOT02).

In one embodiment, the invention encompasses a polypeptide comprising the amino acid sequence of SEQ ID NO:1, as shown in FIGS. 1A, 1B, and 1C. HARP-1 is 199 amino acids in length and has four potential casein kinase II phosphorylation sites at residues S111, S112, S151, and S176; three potential N-myristoylation sites at residues G39, G42, and G84; two potential protein kinase C phosphorylation sites at residues S43 and S67; two potential tyrosine kinase phosphorylation sites at residues Y12 and Y158; and a potential GTP-binding site motif A at residues G39-46. PRINTS identified three motifs associated with GTP-binding proteins comprised of residues D34, I89, and L135. PFAM identified significant sequence identity with the Arf family of monomeric G-proteins. As shown in FIG. 2, HARP-1 has chemical and structural similarity with human ARF6 (GI 178989; SEQ ID NO:14). In particular, HARP-1 and human ARF6 share 27% identity. A region of unique sequence in HARP-1 from about amino acid 129 to about amino acid 134 is encoded by a fragment of SEQ ID NO:3 from about nucleotide 469 to about nucleotide 486. Northern analysis shows the expression of this sequence in libraries of which 50% show inflammation, and all of which are derived from epithelial tissues.

Nucleic acids encoding the HARP-2 of the present invention were first identified in Incyte Clone 1333754 from the colon cDNA library (COLNNOT13) using a computer search, e.g., BLAST, for amino acid sequence alignments. A consensus sequence, SEQ ID NO:4, was derived from the following overlapping and/or extended nucleic acid sequences: Incyte Clones 2614213H1 (GBLANOT01), 2073315F6 (ISLTNOT01), 1802032H1 and 1802320F6 (COLNNOT27), and 1333754 (COLNNOT13).

In one embodiment, the invention encompasses a polypeptide comprising the amino acid sequence of SEQ ID NO:2, as shown in FIGS. 2A, 2B, and 2C. HARP-2 is 192 amino acids in length and has a potential N-glycosylation site at residue N57; three potential casein kinase II phosphorylation sites at residues T61, T132, and S181; one potential cAMP- and cGMP-dependent protein kinase phosphorylation site at residue T172; four potential N-myristoylation sites at residues G2, G20, G129, and G163; three potential protein kinase C phosphorylation sites at residues T92, S100, and S147; a potential tyrosine kinase phosphorylation site at residue Y152; and a potential GTP-binding site motif A at residues G20–27. PRINTS identified four motifs associated with GTP-binding proteins comprised of residues Q15, M71, V116, and R149; and two motifs associated with G-protein a-subunits comprised of residues Q15, L60, and V119. PFAM identified significant sequence identity with the Arf family of monomeric G-proteins. As shown in FIG. 4, HARP-2 has chemical and structural similarity with human ARF6 (GI 178989; SEQ ID NO:14). In particular, HARP-2 and human ARF6 share 41 % identity, have similar molecular mass (21.6 kDa and 20.1 kDa, respectively) and isoelectric points (8.72 and 8.97, respectively), and share a potential N-myristoylation site at residue G2. A region of unique sequence in HARP-2 from about amino acid 111 to about amino acid 117 is encoded by a fragment of SEQ ID NO:4 from about nucleotide 502 to about nucleotide 522. Northern analysis shows the expression of this sequence in libraries of which 75% are associated with inflammation and all of which are derived from the gastrointestinal endothelium.

The invention also encompasses HARP variants. A preferred HARP variant is one which has at least about 80%, more preferably at least about 90%, and most preferably at least about 95% amino acid sequence identity to the HARP amino acid sequence, and which contains at least one functional or structural characteristic of HARP.

The invention also encompasses polynucleotides which encode HARP. In a particular embodiment, the invention encompasses a polynucleotide sequence comprising the sequence of SEQ ID NO:3, as shown in FIG. 1A, 1B, and 1C, which encodes a HARP-1. In another embodiment, the invention encompasses the polynucleotide sequence comprising the sequence of SEQ ID NO:4, as shown in FIG. 2A, 2B, and 2C, which encodes a HARP-2.

The invention also encompasses a variant of a polynucleotide sequence encoding HARP. In particular, such a variant polynucleotide sequence will have at least about 70%, more preferably at least about 85%, and most preferably at least about 95% polynucleotide sequence identity to the polynucleotide sequence encoding HARP. A particular aspect of the invention encompasses a variant of SEQ ID NO:3 which has at least about 70%, more preferably at least about 85%, and most preferably at least about 95% polynucleotide sequence identity to SEQ ID NO:3. The invention further encompasses a polynucleotide variant of SEQ ID NO:4 having at least about 70%, more preferably at least about 85%, and most preferably at least about 95% polynucleotide sequence identity to SEQ ID NO:4. Any one of the polynucleotide variants described above can encode an amino acid sequence which contains at least one functional or structural characteristic of HARP.

It will be appreciated by those skilled in the art that as a result of the degeneracy of the genetic code, a multitude of polynucleotide sequences encoding HARP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HARP, and all such variations are to be considered as being specifically disclosed.

Although nucleotide sequences which encode HARP and its variants are preferably capable of hybridizing to the nucleotide sequence of the naturally occurring HARP under appropriately selected conditions of stringency, it may be advantageous to produce nucleotide sequences encoding HARP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HARP and its derivatives without altering the encoded amino acid sequences include the production of RNA transcripts having more desirable properties, such as a greater half-life, than transcripts produced from the naturally occurring sequence.

The invention also encompasses production of DNA sequences which encode HARP and HARP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HARP or any fragment thereof.

Also encompassed by the invention are polynucleotide sequences that are capable of hybridizing to the claimed polynucleotide sequences, and, in particular, to those shown in SEQ ID NO:3, SEQ ID NO:4, a fragment of SEQ ID NO:3, or a fragment of SEQ ID NO:4, under various conditions of stringency. (See, e.g., Wahl, G. M. and S. L. Berger (1987) Methods Enzymol. 152: 399–407; Kimmel, A. R. (1987) Methods Enzymol. 152: 507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50 % formamide, and 200 µg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE® (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE™ Amplification System (GIBCO BRL, Gaithersburg, Md.). Preferably, sequence preparation is automated with machines such as the Hamilton Micro Lab 2200 (Hamilton, Reno, Nev.), Peltier Thermal Cycler (PTC200; MJ Research, Watertown, Mass.) and the ABI Catalyst 800 (Perkin Elmer). Sequencing is then carried out using either ABI 373 or 377 DNA Sequencing Systems (Perkin Elmer) or capillary electrophoresis (Molecular Dynamics). The resulting sequences are analyzed using a variety of alogorithms which are well known in the art. (See, e.g., Ausubel, supra, ch. 7.7; and Meyers, R. A. (1995) *Molecular Biology and Biotechnology*, Wiley VCH, Inc., New York, N.Y., pp. 856–853.)

The nucleic acid sequences encoding HARP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2: 318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16: 8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1: 111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19: 3055–306). Additionally, one may use PCR, nested primers, and PromoterFinder™ libraries to walk genomic DNA (Clontech, Palo Alto, Calif.). This procedure avoids the need to screen libraries and is useful in finding intron/exon junctions. For all PCR-based methods, primers may be designed using commercially available software, such as OLIGO™ 4.06 Primer Analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode HARP may be cloned in recombinant DNA molecules that direct expression of HARP, or fragments or functional equivalents thereof, in appropriate host cells. Due to the inherent degeneracy of the genetic code, other DNA sequences which encode substantially the same or a functionally equivalent amino acid sequence may be produced and used to express HARP.

The nucleotide sequences of the present invention can be engineered using methods generally known in the art in order to alter HARP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding HARP may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, HARP itself or a fragment thereof may be synthesized using chemical methods. For example, peptide synthesis can be performed using various solid-phase techniques. (See, e.g., Roberge, J. Y. et al. (1995) Science 269: 202–204.) Automated synthesis may be achieved using the ABI 43 1A Peptide Synthesizer (Perkin Elmer). Additionally, the amino acid sequence of HARP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182: 392–421.) The composition of the synthetic peptides may be confirmed by amino acid analysis or by sequencing. (See, e.g., Creighton, T. (1984) *Proteins, Structures and Molecular Properties*, WH Freeman and Co., New York, N.Y.)

In order to express a biologically active HARP, the nucleotide sequences encoding HARP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding HARP. Such elements may vary in their strength and specificity. Specific initiation signals may also be used to achieve more efficient translation of sequences encoding HARP. Such signals include the ATG initiation codon and adjacent sequences, e.g. the Kozak sequence. In cases where sequences encoding HARP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20: 125–162.)

Methods which are well known to those skilled in the art may be used to construct expression vectors containing sequences encoding HARP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding HARP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding HARP. For example, routine cloning, subcloning, and propagation of polynucleotide sequences encoding HARP can be achieved using a multifunctional *E. coli* vector such as Bluescript® (Stratagene) or pSport1™ plasmid (GIBCO BRL). Ligation of sequences encoding HARP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264: 5503–5509.) When large quantities of HARP are needed, e.g. for the production of antibodies, vectors which direct high level expression of HARP may be used. For example, vectors containing the strong, inducible T5 or T7 bacteriophage promoter may be used.

Yeast expression systems may be used for production of HARP. A number of vectors containing constitutive or inducible promoters, such as alpha factor, alcohol oxidase, and PGH, may be used in the yeast *Saccharomyces cerevi-* siae or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153: 516–54; Scorer, C. A. et al. (1994) Bio/Technology 12: 181–184.)

Plant systems may also be used for expression of HARP. Transcription of sequences encoding HARP may be driven viral promoters, e.g., the 35S and 19S promoters of CaMV used alone or in combination with the omega leader sequence from TMV. (Takamatsu, N. (1987) EMBO J. 6: 307–311.) Alternatively, plant promoters such as the small subunit of RUBISCO or heat shock promoters may be used. (See, e.g., Coruzzi, G. et al. (1984) EMBO J. 3: 1671–1680; Broglie, R. et al. (1984) Science 224: 838–843; and Winter, J. et al. (1991) Results Probl. Cell Differ. 17: 85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding HARP may be ligated into an adenovirus transcription/translation complex consisting of the late promoter and tripartite leader sequence. Insertion in a non-essential E1 or E3 region of the viral genome may be used to obtain infective virus which expresses HARP in host cells. (See, e.g., Logan, J. and T. Shenk (1984) Proc. Natl. Acad. Sci. 81: 3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of HARP in cell lines is preferred. Folines using expression vectors which m be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk or apr⁻ cells, respectively. (See, e.g., Wigler, M. et al. (1977) Cell 11: 223–232; and Lowy, I. et al. (1980) Cell 22: 817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77: 3567–3570; Colbere-Garapin, F. et al (1981) J. Mol. Biol. 150: 1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85: 8047–8051.) Visible markers, e.g., anthocyanins, green fluorescent proteins (GFP) (Clontech, Palo Alto, Calif.), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55: 121–131.)

Although the presence/absence of marker gene expression suggests that the gene of interest is also present, the presence and expression of the gene may need to be confirmed. For example, if the sequence encoding HARP is inserted within a marker gene sequence, transformed cells containing sequences encoding HARP can be identified by the absence of marker gene function. Alternatively, a marker gene can be placed in tandem with a sequence encoding HARP under the control of a single promoter. Expression of the marker gene in response to induction or selection usually indicates expression of the tandem gene as well.

In general, host cells that contain the nucleic acid sequence encoding HARP and that express HARP may be identified by a variety of procedures known to those of skill in the art. These procedures include, but are not limited to, DNA—DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of HARP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HARP is preferred, but a competitive binding assay may be employed. These and other assays are well known in the art. (See, e.g., Hampton, R. et al. (1990) *Serological Methods, a Laboratory Manual*, APS Press, St Paul, Minn., Section IV; Coligan, J. E. et al. (1997 and periodic supplements) *Current Protocols in Immunology*, Greene Pub. Associates and Wiley-Interscience, New York, N.Y.; and Maddox, D. E. et al. (1983) J. Exp. Med. 158: 1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HARP include oligolabeling, nick translation, end-labeling, or PCR amplification using a labeled nucleotide. Alternatively, the sequences encoding HARP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HARP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode HARP may be designed to contain signal sequences which direct secretion of HARP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding HARP may be ligated to a heterologous sequence resulting in translation of a fusion protein in any of the aforementioned host systems. For example, a chimeric HARP protein containing a heterologous moiety that can be recognized by a commercially available antibody may facilitate the screening of peptide libraries for inhibitors of HARP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HARP encoding sequence and the heterologous protein sequence, so that HARP may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled HARP may be achieved in vitro using the TNT™ rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of HARP may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431 A Peptide Synthesizer (Perkin Elmer). Various fragments of HARP may be synthesized separately and then combined to produce the full length molecule.

Therapeutics

Chemical and structural similarity exists between HARP-1 and ADP-ribosylation factor-6 from human (GI 178989). In addition, HARP-1 is expressed in epithelial tissues, 50% of which are inflamed. Therefore, HARP-1 appears to play a role in secretory and epithelial disorders, including those disorders associated with inflammation.

Chemical and structural similarity exists between HARP-2 and ADP-ribosylation factor-6 from human (GI 178989). In addition, HARP-2 is expressed in gastrointestinal tract epithelial tissues, 75% of which are inflamed. Therefore, HARP-2 appears to play a role in secretory and epithelial disorders, including those disorders associated with inflammation.

Therefore, in one embodiment, HARP or a fragment or derivative thereof may be administered to a subject to treat or prevent an epithelial disorder. Such epithelial disorders can include, but are not limited to, eczema, atopic dermatitis, contact dermatitis, stasis dermatitis, seborrheic dermatitis, psoriasis, lichen planus, pityriasis rosea, acne vulgaris, acne rosacea, pemphigus vulgaris, pemphigus foliaceus, paraneoplastic pemphigus, bullous pemphigoid, herpes gestationis, dermatitis herpetiformis, linear IgA disease, epidermolysis bullosa acquisita, dermatomyositis, lupus erythematosus, scleroderma, and morphea; gastritis, peptic ulcers, cholelithiasis, cholecystitis, pancreatitis, cirrhosis, ulcerative colitis, Crohn's disease, and irritable bowel syndrome; Addison's disease, Lowe's syndrome, glomerulonephritis, chronic glomerulonephritis, tubulointerstitial nephritis, inherited X-linked nephrogenic diabetes insipidus and autosomal dominant polycystic kidney disease (ADPKD).

In another embodiment, a vector capable of expressing HARP-1 or a fragment or derivative thereof may be administered to a subject to treat or prevent an epithelial disorder including, but not limited to, those described above.

In a further embodiment, a pharmaceutical composition comprising a substantially purified HARP-1 in conjunction with a suitable pharmaceutical carrier may be administered to a subject to treat or prevent an epithelial disorder including, but not limited to, those provided above.

In still another embodiment, an agonist which modulates the activity of HARP may be administered to a subject to treat or prevent an epithelial disorder including, but not limited to, those listed above.

In another embodiment, HARP or a fragment or derivative thereof may be administered to a subject to treat or prevent a secretory disorder. Such secretory disorders can include, but are not limited to, cystic fibrosis, glucose-galactose malabsorption syndrome, hypercholesterolemia, diabetes insipidus, hyper- and hypoglycemia, Grave's disease, goiter, and Cushing's disease; other conditions associated with abnormal vesicle trafficking, including acquired immunodeficiency syndrome (AIDS); allergies including hay fever, asthma, and urticaria (hives); autoimmune hemolytic anemia; multiple sclerosis; myasthenia gravis; rheumatoid and osteoarthritis; Chediak-Higashi and Sjogren's syndromes; toxic shock syndrome; traumatic tissue damage; and viral, bacterial, fungal, helminthic, and protozoal infections.

In another embodiment, a vector capable of expressing HARP-1 or a fragment or derivative thereof may be administered to a subject to treat or prevent a secretory disorder including, but not limited to, those described above.

In a further embodiment, a pharmaceutical composition comprising a substantially purified HARP-1 in conjunction with a suitable pharmaceutical carrier may be administered to a subject to treat or prevent a secretory disorder including, but not limited to, those provided above.

In still another embodiment, an agonist which modulates the activity of HARP may be administered to a subject to treat or prevent a secretory disorder including, but not limited to, those listed above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HARP may be produced using methods which are generally known in the art. In particular, purified HARP may be used to produce antibodies or to screen libraries of pharmaceutical agents to identify those which specifically bind HARP. Antibodies to HARP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HARP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HARP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HARP amino acids may be fused with those of another protein, such as KLH, and antibodies to the chimeric molecule may be produced.

Monoclonal antibodies to HARP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256: 495–497; Kozbor, D. et al. (1985) J. Immunol. Methods 81: 31–42; Cote, R. J. et al. (1983) Proc. Natl. Acad. Sci. 80: 2026–2030; and Cole, S. P. et al. (1984) Mol. Cell Biol. 62: 109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81: 6851–6855; Neuberger, M. S. et al. (1984) Nature 312: 604–608; and Takeda, S. et al. (1985) Nature 314: 452–454.) Alternatively, techniques described for the production of single chain antibodies may be adapted, using methods known in the art, to produce HARP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88: 10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349: 293–299.)

Antibody fragments which contain specific binding sites for HARP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246: 1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HARP and its specific antibody. A two-site, monoclonal-based immunoassay utilizing monoclonal antibodies reactive to two non-stimulated HARP epitopes is preferred, but a competitive binding assay may also be employed. (Maddox, supra.)

In another embodiment of the invention, the polynucleotides encoding HARP, or any fragment or complement thereof, may be used for therapeutic purposes. In one aspect, the complement of the polynucleotide encoding HARP may be used in situations in which it would be desirable to block the transcription of the mRNA. In particular, cells may be transformed with sequences complementary to polynucleotides encoding HARP. Thus, complementary molecules or fragments may be used to modulate HARP activity, or to achieve regulation of gene function. Such technology is now well known in the art, and sense or antisense oligonucleotides or larger fragments can be designed from various locations along the coding or control regions of sequences encoding HARP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding HARP. (See, e.g., Sambrook, supra; and Ausubel, supra.)

Genes encoding HARP can be turned off by transforming a cell or tissue with expression vectors which express high levels of a polynucleotide, or fragment thereof, encoding HARP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HARP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HARP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HARP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15: 462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HARP, antibodies to HARP, and mimetics, agonists, antagonists, or inhibitors of HARP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HARP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HARP or fragments thereof, antibodies of HARP, and agonists, antagonists or inhibitors of HARP, which ameliorates the symptoms or condition. Therapeutic efficacy and toxicity may be determined by standard pharmaceutical procedures in cell cultures or with experimental animals, such as by calculating the $ED_{50}$. (the dose therapeutically effective in 50% of the population) or $LD_5$. (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HARP may be used for the diagnosis of disorders characterized by expression of HARP, or in assays to monitor patients being treated with HARP or agonists, antagonists, or inhibitors of HARP. Antibodies useful for diagnostic purposes may be prepared in the same manner as described above for therapeutics. Diagnostic assays for HARP include methods which utilize the antibody and a label to detect HARP in human body fluids or in extracts of cells or tissues. The antibodies may be used with or without modification, and may be labeled by covalent or noncovalent attachment of a reporter molecule. A wide variety of reporter molecules, several of which are described above, are known in the art and may be used.

A variety of protocols for measuring HARP, including ELISAs, RIAs, and FACS, are known in the art and provide a basis for diagnosing altered or abnormal levels of HARP expression. Normal or standard values for HARP expression are established by combining body fluids or cell extracts taken from normal mammalian subjects, preferably human, with antibody to HARP under conditions suitable for complex formation The amount of standard complex formation may be quantitated by various methods, preferably by photometric means. Quantities of HARP expressed in subject, control, and disease samples from biopsied tissues are compared with the standard values. Deviation between standard and subject values establishes the parameters for diagnosing disease.

In another embodiment of the invention, the polynucleotides encoding HARP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HARP may be correlated with disease. The diagnostic assay may be used to determine absence, presence, and excess expression of HARP, and to monitor regulation of HARP levels during therapeutic intervention.

In one aspect, hybridization with PCR probes which are capable of detecting polynucleotide sequences, including genomic sequences, encoding HARP or closely related molecules may be used to identify nucleic acid sequences which encode HARP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HARP, allelic variants, or related sequences.

Probes may also be used for the detection of related sequences, and should preferably have at least 50% sequence identity to any of the HARP encoding sequences. The hybridization probes of the subject invention may be DNA or RNA and may be derived from the sequence of SEQ ID NO:3, SEQ ID NO:4, or from genomic sequences including promoters, enhancers, and introns of the HARP gene.

Means for producing specific hybridization probes for DNAs encoding HARP include the cloning of polynucleotide sequences encoding HARP or HARP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HARP may be used for the diagnosis of a disorder associated with expression of HARP. Examples of such a disorder include, but are not limited to, epithelial disorders, such as eczema, atopic dermatitis, contact dermatitis, stasis dermatitis, seborrheic dermatitis, psoriasis, lichen planus, pityriasis rosea, acne vulgaris, acne rosacea, penphigus vulgaris, penphigus foliaceus, paraneoplastic pemphigus, bullous pemphigoid, herpes gestationis, dermatitis herpetiformis, linear IgA disease, epidermolysis bullosa acquisita, dermatomyositis, lupus erythematosus, scleroderma, and morphea; gastritis, peptic ulcers, cholelithiasis, cholecystitis, pancreatitis, cirrhosis, ulcerative colitis, Crohn's disease, and irritable bowel syndrome; Addison's disease, Lowe's syndrome, glomerulonephritis, chronic glomerulonephritis, tubulointerstitial nephritis, inherited X-linked nephrogenic diabetes insipidus and autosomal dominant polycystic kidney disease (ADPKD); and secretory disorders, such as cystic fibrosis, glucose-galactose malabsorption syndrome, hypercholesterolemia, diabetes insipidus, hyper- and hypoglycemia, Grave's disease, goiter, and Cushing's disease; other conditions associated with abnormal vesicle trafficking, including acquired immunodeficiency syndrome (AIDS); allergies including hay fever, asthma, and urticaria (hives); autoimmune hemolytic anemia; multiple sclerosis; myasthenia gravis; rheumatoid and osteoarthritis; Chediak-Higashi and Sjogren's syndromes; toxic shock syndrome; traumatic tissue damage; and viral, bacterial, fungal, helminthic, and protozoal infections. The polynucleotide sequences encoding HARP may be used in Southern or Northern analysis, dot blot, or other membrane-based technologies; in PCR technologies; in dipstick, pin, and ELISA assays; and in microarrays utilizing fluids or tissues from patients to detect altered HARP expression. Such qualitative or quantitative methods are well known in the art.

In a particular aspect, the nucleotide sequences encoding HARP may be useful in assays that detect the presence of associated disorders, particularly those mentioned above. The nucleotide sequences encoding HARP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HARP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HARP, a normal or standard profile for expression is established. This may be accomplished by combining body fluids or cell extracts taken from normal subjects, either animal or human, with a sequence, or a fragment thereof, encoding HARP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

Additional diagnostic uses for oligonucleotides designed from the sequences encoding HARP may involve the use of PCR. These oligomers may be chemically synthesized, generated enzymatically, or produced in vitro. Oligomers will preferably contain a fragment of a polynucleotide encoding HARP, or a fragment of a polynucleotide complementary to the polynucleotide encoding HARP, and will be employed under optimized conditions for identification of a specific gene or condition. Oligomers may also be employed under less stringent conditions for detection or quantitation of closely related DNA or RNA sequences.

Methods which may also be used to quantitate the expression of HARP include radiolabeling or biotinylating nucleotides, coamplification of a control nucleic acid, and interpolating results from standard curves. (See, e.g., Melby, P. C. et al. (1993) J. Immunol. Methods 159: 235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93: 10614–10619; Baldeschweiler et al. (1995) PCT application W095/251116; Shalon, D. et al. (1995) PCT application WO95/35505; Heller, R. A. et al. (1997) Proc. Natl. Acad. Sci. 94: 2150–2155; and Heller, M. J. et al. (1997) U.S. Pat. No. 5,605,662.)

In another embodiment of the invention, nucleic acid sequences encoding HARP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial PI constructions, or single chromosome cDNA libraries. (See, e.g., Price, C. M. (1993) Blood Rev. 7: 127–134; and Trask, B. J. (1991) Trends Genet. 7: 149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding HARP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336: 577–580.) The nucleotide sequence of the subject invention may also be used to detect differences in the chromosomal location due to translocation, inversion, etc., among normal, carrier, or affected individuals.

In another embodiment of the invention, HARP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HARP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HARP, or fragments thereof, and washed. Bound HARP is then detected by methods well known in the art. Purified HARP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HARP specifically compete with a test compound for binding HARP. In this manner, antibodies can be used to detect the presence of any peptide which shares one or more antigenic determinants with HARP.

In additional embodiments, the nucleotide sequences which encode HARP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction
KERANOTO2

The KERANOT02 cDNA library was constructed from a normal epidermal keratinocyte (NHEK) primary cell line, acquired from Clontech (Palo Alto, Calif.) and obtained from a 30 year-old black female undergoing breast reduction surgery. Epidermal keratinocytes were isolated from the resected tissue and allowed to proliferate before cryopreservation.

COLNNOT13

The COLNNOT13 cDNA library was constructed from ascending colon tissue obtained from a 28-year-old Caucasian male diagnosed with moderate chronic ulcerative colitis. The patient had undergone a temporary ileostomy.

KERANOT02 and COLNNOT13

The frozen tissue was homogenized and lysed using a Brinkmann Homogenizer Polytron PT-3000 (Brinkmann Instruments, Westbury N.J.). The lysate was centrifuged over a 5.7 M CsCl cushion using a Beckman SW28 rotor in a Beckman L8-70M Ultracentrifuge (Beckman Instruments) for 18 hours at 25,000 rpm at ambient temperature. RNA was extracted with phenol chloroform pH 4.0, precipitated using 0.3 M sodium acetate and 2.5 volumes of ethanol, resuspended in DEPC-treated water and treated with DNase at 37° C. RNA extraction and precipitation were repeated as before. Poly(A+) RNA was isolated using the Qiagen Oligotex kit (QIAGEN, Inc., Chatsworth, Calif.).

Poly(A+) RNA was used for cDNA synthesis and library construction according to the recommended protocols in the SuperScript™ plasmid system (Life Technologies, Inc., Gaithersburg, Md.). cDNAs were fractionated on a Sepharose CL4B column (catalog #275105, Pharmacia) and those cDNAs exceeding 400 bp were ligated into cloning vector, pSPORT (Life Technologies, Inc.) or pINCY (Incyte Pharmaceuticals, Inc., Palo Alto, Calif.) for KERANOT02 and COLNNOT13, respectively, and subsequently transformed into DH5α™ competent cells (Cat. #18258-012, Life Technologies, Inc.).

II. Isolation and Sequencing of cDNA Clones

Plasmid DNA was released from the cells and purified using the Miniprep Kit (Catalog #77468; Advanced Genetic Technologies Corporation, Gaithersburg Md.) for the KERANOT02 library and the REAL Prep 96 plasmid kit (Catalog #26173, QIAGEN, Inc.) for the COLNNOT13 library. The recommended protocols were employed except for the following changes: 1) the bacteria were cultured in 1 ml of sterile Terrific Broth (Life Technologies, Inc.) with carbenicillin at 25 mg/L and glycerol at 0.4%; 2) after the cultures were incubated for 19 hours, the cells were lysed with 0.3 ml of lysis buffer; and 3) following isopropanol precipitation, the plasmid DNA pellets were resuspended in 0.1 ml of distilled water. The DNA samples were stored at 4° C.

The cDNAs were sequenced by the method of Sanger et al. (1975, *J. Mol. Biol.* 94: 441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems, and the reading frame was determined.

III. Similarity Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of similarity using BLAST (Basic Local Alignment Search Tool). (See, e.g., Altschul, S. F. (1993) J. Mol. Evol 36: 290–300; and Altschul et al. (1990) J. Mol. Biol. 215: 403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5: 35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for similarity.

Additionally, sequences identified from cDNA libraries may be analyzed to identify those gene sequences encoding conserved protein motifs using an appropriate analysis program, e.g., BLOCKS. BLOCKS is a weighted matrix analysis algorithm based on short amino acid segments, or blocks, compiled from the PROSITE database. (Bairoch, A. et al. (1997) Nucleic Acids Res. 25: 217–221.) The BLOCKS algorithm is useful for classifying genes with unknown functions. (Henikoff, S. and Henikoff, G. J., Nucleic Acids Research (1991) 19: 6565–6572.) Blocks, which are 3 to 60 amino acids in length, correspond to the most highly conserved regions of proteins. The BLOCKS algorithm compares a query sequence with a weighted scoring matrix of blocks in the BLOCKS database. Blocks in the BLOCKS database are calibrated against protein sequences with known functions from the SWISS-PROT database to determine the stochastic distribution of matches. Similar databases such as PRINTS, a protein fingerprint database, are also searchable using the BLOCKS algorithm. (Attwood, T. K. et al. (1997) J. Chem. Inf. Comput. Sci. 37: 417–424.) PRINTS is based on non-redundant sequences obtained from sources such as SWISS-PROT, GenBank, PIR, and NRL-3D.

The BLOCKS algorithm searches for matches between a query sequence and the BLOCKS or PRINTS database and evaluates the statistical significance of any matches found. Matches from a BLOCKS or PRINTS search can be evaluated on two levels, local similarity and global similarity. The degree of local similarity is measured by scores, and the extent of global similarity is measured by score ranking and probability values. A score of 1000 or greater for a BLOCKS match of highest ranking indicates that the match falls within the 0.5 percentile level of false positives when the matched block is calibrated against SWISS-PROT. Likewise, a probability value of less than $1.0 \times 10^{-3}$ indicates that the match would occur by chance no more than one time in every 1000 searches. Only those matches with a cutoff score of 1000 or greater and a cutoff probability value of $1.0 \times 10^{-3}$ or less are considered in the functional analyses of the protein sequences in the Sequence Listing.

Nucleic and amino acid sequences of the Sequence Listing may also be analyzed using PFAM. PFAM is a Hidden Markov Model (HMM) based protocol useful in protein family searching. HMM is a probabilistic approach which analyzes consensus primary structures of gene families. (See, e.g., Eddy, S. R. (1996) Cur. Opin. Str. Biol. 6: 361–365.)

The PFAM database contains protein sequences of 527 protein families gathered from publicly available sources, e.g., SWISS-PROT and PROSITE. PFAM searches for well characterized protein domain families using two high-quality alignment routines, seed alignment and full alignment. (See, e.g., Sonnhammer, E. L. L. et al. (1997) Proteins 28: 405–420.) The seed alignment utilizes the hmmls program, a program that searches for local matches, and a non-redundant set of the PFAM database. The full alignment utilizes the hmmfs program, a program that searches for multiple fragments in long sequences, e.g., repeats and motifs, and all sequences in the PFAM database. A result or score of 100 "bits" can signify that it is $2^{100}$-fold more likely that the sequence is a true match to the model or comparison sequence. Cutoff scores which range from 10 to 50 bits are generally used for individual protein families using the SWISS-PROT sequences as model or comparison sequences.

Two other algorithms, SIGPEPT and TM, both based on the HMM algorithm described above (see, e.g., Eddy, supra; and Sonnhammer, supra), identify potential signal sequences and transmembrane domains, respectively. SIGPEPT was created using protein sequences having signal sequence annotations derived from SWISS-PROT. It contains about 1413 non-redundant signal sequences ranging in length from 14 to 36 amino acid residues. TM was created similarly using transmembrane domain annotations. It contains about 453 non-redundant transmembrane sequences encompassing 1579 transmembrane domain segments. Suitable HMM models were constructed using the above sequences and were refined with known SWISS-PROT signal peptide sequences or transmembrane domain sequences until a high correlation coefficient, a measurement of the correctness of the analysis, was obtained. Using the protein sequences from the SWISS-PROT database as a test set, a cutoff score of 11 bits, as determined above, correlated with 91–94% true-positives and about 4.1% false-positives, yielding a correlation coefficient of about 0.87–0.90 for SIGPEPT. A score of 11 bits for TM will typically give the following results: 75% true positives; 1.72% false positives; and a correlation coefficient of 0.76. Each search evaluates the statistical significance of any matches found and reports only those matches that score at least 11 bits.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or similar.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis are reported as a list of libraries in which the transcript encoding HARP occurs. Abundance and percent abundance are also reported. Abundance directly reflects the number of times a particular transcript is represented in a cDNA library, and percent abundance is abundance divided by the total number of sequences examined in the cDNA library.

V. Extension of HARP Encoding Polynucleotides

The nucleic acid sequences of Incyte Clones 823143 and 1333754 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO™ 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer—primer dimerizations was avoided.

Selected human cDNA libraries (GIBCO BRL) were used to extend the sequence. If more than one extension is necessary or desired, additional sets of primers are designed to further extend the known region.

High fidelity amplification was obtained by following the instructions for the XL-PCR™ kit (Perkin Elmer) and thoroughly mixing the enzyme and reaction mix. PCR was performed using the Peltier Thermal Cycler (PTC200; M.J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK™ (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2x carb). The following day, several colonies were randomly picked from each plate and cultured in 150 µl of liquid LB/2x carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3x) containing 4 units of rTth DNA polymerase, a vector primer, and one or both of the gene specific primers used for the extension reaction were added to each well.

Amplification was performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:3 and SEQ ID NO:4 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:3 and SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO™ 4.06 software (National Biosciences) and labeled by combining 50 pmol of each oligomer, 250 µCi of [$\gamma$-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex™ G-25 superfine size exclusion dextran bead column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN, Boston, Mass.).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270: 467–470; and Shalon, D. et al. (1996) Genome Res. 6: 639–645.) Fluorescent probes are prepared and used for hybridization to the elements on the substrate. The substrate is analyzed by procedures described above.

VIII. Complementary Polynucleotides

Sequences complementary to the HARP-encoding sequences, or any parts thereof, are used to detect, decrease, or inhibit expression of naturally occurring HARP. Although use of oligonucleotides comprising from about 15 to 30 base pairs is described, essentially the same procedure is used with smaller or with larger sequence fragments. Appropriate oligonucleotides are designed using OLIGO™ 4.06 software and the coding sequence of HARP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HARP-encoding transcript.

IX. Expression of HARP

Expression and purification of HARP is achieved using bacterial or virus-based expression systems. For expression of HARP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21 (DE3). Antibiotic resistant bacteria express HARP upon induction with isopropyl beta-D-thiogalactopyranoside (IPTG). Expression of HARP in eukaryotic cells is achieved by infecting insect or mammalian cell lines with recombinant *Autoraphica californica* nuclear polyhedrosis virus (AcMNPV), commonly known as baculovirus. The nonessential polyhedrin gene of baculovirus is replaced with cDNA encoding HARP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91: 3224–3227; Sandig, V. et al. (1996) Hum. Gene Ther. 7: 1937–1945.)

In most expression systems, HARP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Pharmacia, Piscataway, N.J.). Following purification, the GST moiety can be proteolytically cleaved from HARP at specifically engineered sites. FLAG, an 8-amino acid peptide, enables immunoaffinity purification using commercially available monoclonal and polyclonal anti-FLAG antibodies (Eastman Kodak, Rochester, N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) *Current Protocols in Molecular Biology*, John Wiley & Sons, New York, N.Y., ch 10, 16. Purified HARP obtained by these methods can be used directly in the following activity assay.

X. Demonstration of HARP Activity

The activity of HARP is demonstrated by its ability to activate phospholipase D (hPLD2) as described by Lopez et al. (1998; J. Biol. Chem. 273: 12846–12852). Samples containing HARP are incubated on ice in solution C (50 mM HEPES (pH 7.5), 80 mM KCl, 3 mM $MgCl_2$, 2 mM $CaCl_2$, 1 mM dithiothreitol) containing 5 µg of hPLD2 membranes and 30 MM GTPγS. Lipid substrate is added in the form of phospholipid dispersions composed of phosphatidylethanolamine, $PIP_2$, and dipalmitoyl phosphatidylcholine (PC) in a molar ratio of 16:1.4:1, respectively. L-α-dipalmitoyl [choline-methyl-$^3$H] is added to give 50,000 cpm/assay. The substrate is prepared by drying the lipids under a stream of nitrogen, and resuspending them by sonication in solution C without divalent cations. Upon substrate addition the samples are incubated 15 min at 37° C. in a volume of 150 µl. Reactions are terminated by the addition of 1 ml of $CHCl_3$/methanol/HCl (50:50:0.3, v/v/v) and 350 µl of 1 M HCl, 5 mM EGTA. The amount of [$^3$H]choline released into the aqueous phase, quantified by scintillation counting, is proportional to the amount of activated PLD and the amount of HARP in the sample.

XI. Functional Assays

HARP function is assessed by expressing the sequences encoding HARP at physiologically elevated levels in mammalian cell culture systems. cDNA is subcloned into a mammalian expression vector containing a strong promoter that drives high levels of cDNA expression. Vectors of choice include pCMV SPORT™ (Life Technologies, Gaithersburg, Md.) and pCR™ 3.1 (Invitrogen, Carlsbad, Calif., both of which contain the cytomegalovirus promoter. 5–10 µg of recombinant vector are transiently transfected into a human cell line, preferably of endothelial or hematopoietic origin, using either liposome formulations or electroporation. 1–2 µg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of HARP on gene expression can be assessed using highly purified populations of cells transfected with sequences encoding HARP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding HARP and other genes of interest can be analyzed by Northern analysis or microarray techniques.

XII. Production of HARP Specific Antibodies

HARP substantially purified using polyacrylamide gel electrophoresis (PAGE)(see, e.g., Harrington, M. G. (1990) Methods Enzymol. 182: 488–495), or other purification techniques, is used to immunize rabbits and to produce antibodies using standard protocols.

Alternatively, the HARP amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring HARP Using Specific Antibodies

Naturally occurring or recombinant HARP is substantially purified by immunoaffinity chromatography using antibodies specific for HARP. An immunoaffinity column is constructed by covalently coupling anti-HARP antibody to an activated chromatographic resin, such as CNBr-activated Sepharose (Pharmacia & Upjohn). After the coupling, the resin is blocked and washed according to the manufacturer's instructions.

Media containing HARP are passed over the immunoaffinity column, and the column is washed under conditions that allow the preferential absorbance of HARP (e.g., high ionic strength buffers in the presence of detergent). The column is eluted under conditions that disrupt antibody/HARP binding (e.g., a buffer of pH 2 to pH 3, or a high concentration of a chaotrope, such as urea or thiocyanate ion), and HARP is collected.

XIV. Identification of Molecules Which Interact with HARP

HARP, or biologically active fragments thereof, are labeled with $^{125}$I Bolton-Hunter reagent. (See, e.g., Bolton et al. (1973) Biochem. J. 133: 529.) Candidate molecules previously arrayed in the wells of a multi-well plate are incubated with the labeled HARP, washed, and any wells with labeled HARP complex are assayed. Data obtained using different concentrations of HARP are used to calculate values for the number, affinity, and association of HARP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide comprising SEQ ID NO:1 or SEQ ID NO:2.

2. An isolated and purified polynucleotide which hybridizes under high stringency hybridization conditions and wash conditions of 15 mM NaCl, 1.5 mM trisodium citrate and 0.1% SDS at 68° C. to the polynucleotide of claim 1.

3. An isolated and purified polynuclceotide sequence having a sequence which is completely complementary to the polynucleotide sequence of claim 1.

4. An isolated and purified polynucleotide comprising a polynucleotide sequence of SEQ ID NO:3 or SEQ ID NO:4.

5. An isolated and purified polynucleotide having a sequence which is complementary to the polynucleotide of claim 4.

6. An expression vector comprising at least a fragment of the polynucleotide of claim 1.

7. A host cell comprising the expression vector of claim 6.

8. A method for producing a polypeptide comprising the amino acid sequence of SEQ ID NO:1 or SEQ ID NO:2, the method comprising the steps of:

a) culturing the host cell of claim 7 under conditions suitable for the expression of the polypeptide; and b) recovering the polypeptide from the host cell culture.

9. A method for detecting a polynucleotide encoding the polypeptide comprising the amino acid sequence of SEQ ID NO:1 or SEQ ID NO:2 in a sample, the method comprising the steps of:

(a) hybridizing the polynucleotide of claim 3 to at least one of the nucleic acids in the sample, thereby forming a hybridization complex; and (b) detecting the hybridization complex, wherein the presence of the hybridization complex correlates with the presence of the polynucleotide encoding the polypeptide in the sample.

10. The method of claim 9 wherein the nucleic acids of the biological sample are amplified by the polymerase chain reaction prior to the hybridizing step.

* * * * *

```
                           SEQUENCE LISTING (1) GENERAL INFORMATION:

(iii) NUMBER OF SEQUENCES: 14

(2) INFORMATION FOR SEQ ID NO:       1:

(i) SEQUENCE CHARACTERISTICS:
            (A) LENGTH: 199 amino acids
            (B) TYPE: amino acid
            (C) STRANDEDNESS: single
            (D) TOPOLOGY: linear (vii) IMMEDIATE SOURCE:
            (A) LIBRARY: KERANOT02
            (B) CLONE: 823143

(xi) SEQUENCE DESCRIPTION: SEQ ID NO: 1 :

Met Ser Asp Leu Arg Ile Thr Glu Ala Phe Leu Tyr Met Asp Tyr
                 5                  10                  15

Leu Cys Phe Arg Ala Leu Cys Cys Lys Gly Pro Pro Ala Arg
                20                  25                  30

Pro Glu Tyr Asp Leu Val Cys Ile Gly Leu Thr Gly Ser Gly Lys
                35                  40                  45

Thr Ser Leu Leu Ser Lys Leu Cys Ser Glu Ser Pro Asp Asn Val
                50                  55                  60

Val Ser Thr Thr Gly Phe Ser Ile Lys Ala Val Pro Phe Gln Asn
                65                  70                  75

Ala Ile Leu Asn Val Lys Glu Leu Gly Gly Ala Asp Asn Ile Arg
                80                  85                  90

Lys Tyr Trp Ser Arg Tyr Tyr Gln Gly Ser Gln Gly Val Ile Phe
                95                 100                 105

Val Leu Asp Ser Ala Ser Ser Glu Asp Leu Glu Ala Ala Arg
               110                 115                 120

Asn Glu Leu His Ser Ala Leu Gln His Pro Gln Leu Cys Thr Leu
               125                 130                 135

Pro Phe Leu Ile Leu Ala Asn His Gln Asp Lys Pro Ala Ala Arg
               140                 145                 150

Ser Val Gln Glu Xaa Lys Lys Tyr Phe Glu Leu Glu Pro Leu Xaa
               155                 160                 165

Arg Gly Lys Arg Trp Ile Leu Gln Pro Cys Ser Leu Asp Asp Leu
               170                 175                 180

Asp Gly Xaa Xaa Arg Pro Xaa Leu Ser Xaa Xaa Xaa Xaa Val Arg
               185                 190                 195

Arg Lys Arg Pro (2) INFORMATION FOR SEQ ID NO:       2:

(i) SEQUENCE CHARACTERISTICS:
            (A) LENGTH: 192 amino acids
```

```
        (B) TYPE: amino acid
        (C) STRANDEDNESS: single
        (D) TOPOLOGY: linear (vii) IMMEDIATE SOURCE:
        (A) LIBRARY: COLNNOT13
        (B) CLONE: 1333754

(xi) SEQUENCE DESCRIPTION: SEQ ID NO: 2 :

Met Gly Ser Leu Gly Ser Lys Asn Pro Gln Thr Lys Gln Ala Gln
                5                   10                  15

Val Leu Leu Leu Gly Leu Asp Ser Ala Gly Lys Ser Thr Leu Leu
                20                  25                  30

Tyr Lys Leu Lys Leu Ala Lys Asp Ile Thr Thr Ile Pro Thr Ile
                35                  40                  45

Gly Phe Asn Val Glu Met Ile Glu Leu Glu Arg Asn Leu Ser Leu
                50                  55                  60

Thr Val Trp Asp Val Gly Gly Gln Glu Lys Met Arg Thr Val Trp
                65                  70                  75

Gly Cys Tyr Cys Glu Asn Thr Asp Gly Leu Val Tyr Val Val Asp
                80                  85                  90

Ser Thr Asp Lys Gln Arg Leu Glu Glu Ser Gln Arg Gln Phe Glu
                95                  100                 105

His Ile Leu Lys Asn Glu His Ile Lys Asn Val Pro Val Val Leu
                110                 115                 120

Leu Ala Asn Lys Gln Asp Met Pro Gly Ala Leu Thr Ala Glu Asp
                125                 130                 135

Ile Thr Arg Met Phe Lys Val Lys Lys Leu Cys Ser Asp Arg Asn
                140                 145                 150

Trp Tyr Val Gln Pro Cys Cys Ala Leu Thr Gly Glu Gly Leu Ala
                155                 160                 165

Gln Gly Phe Arg Lys Leu Thr Gly Phe Val Lys Ser His Met Lys
                170                 175                 180

Ser Arg Gly Asp Thr Leu Ala Phe Phe Lys Gln Asn
                185                 190

(2) INFORMATION FOR SEQ ID NO:    3:

(i) SEQUENCE CHARACTERISTICS:
        (A) LENGTH: 920 base pairs
        (B) TYPE: nucleic acid
        (C) STRANDEDNESS: single
        (D) TOPOLOGY: linear (vii) IMMEDIATE SOURCE:
        (A) LIBRARY: KERANOT02
        (B) CLONE: 823143

(xi) SEQUENCE DESCRIPTION: SEQ ID NO: 3 :

cttttttcagg ngctgctcgc tcncagccag agacgctgct ttttttttcc gggttcggag    60
ccgttccgga tgctttaggc tgccggatgt ctgatctccg gataactgag gcgtttctgt   120
acatggatta tctgtgtttt agagcacttt gctgcaaggg accaccacct gcacgaccag   180
aatatgacct ggtttgcata ggcctcacag gttctggcaa aaccagtctg ttgtccaaac   240
tctgcagtga aagccccgat aacgtcgtgt cgaccacagg ttttagtatt aaagcagtgc   300
cattccagaa tgccatcttg aatgtaaaag aacttggagg ggctgataac atccggaaat   360
actggagccg ctactaccaa ggatctcaag gggtaatatt tgtattagac agtgcctctt   420
cagaggatga tttagaagct gctagaaatg agctgcactc agctcttcag catccacagt   480
```

```
tatgcacttt  accctttta  atattggcca  atcatcaaga  caagccagca  gctcgctcag    540
tacaagagat  naaaaaatat  tttgaacttg  aaccacttgc  ncgtggaaaa  cgctggattc    600
tacagccctg  ctcactggat  gacctggatg  gcnctgnaag  accagntctc  tcagnngant    660
nnnttgttag  aagaaaaaga  ccatgaagct  gtaagnatgg  tgaaattctg  ggcaaagaaa    720
acagggctcc  ccnaaagggc  cttgaaacct  atcatgttag  tttcctcatt  ttaatnttaa    780
ttttgggnaa  tccagactat  attggggctt  ccggaatcca  antttttccnc  ctggngcatt    840 ttccagactt  ntccatcttc  tcccaattta  aangggaatn  attcctggtn  ggattccgga    900
tggaatttat  cctgnggngc                                                    920

(2) INFORMATION FOR SEQ ID NO:    4:

(i) SEQUENCE CHARACTERISTICS:
          (A) LENGTH: 1005 base pairs
          (B) TYPE: nucleic acid
          (C) STRANDEDNESS: single
          (D) TOPOLOGY: linear (vii) IMMEDIATE SOURCE:
          (A) LIBRARY: COLNNOT13
          (B) CLONE: 1333754

(xi) SEQUENCE DESCRIPTION: SEQ ID NO: 4 :

TAAACACATC  TAGGTTCTTG  TTCTTAGAAT  ACAGCATGAA  GAATTTGCTT  TCTTCTTTCT     60

TCCTAACATT  TTCATGTGAG  ATCCAGAAAG  GACACATTGT  CTCTGGCCAT  TCGAAGAAAG    120

AAAGAAAGAA  AGAAAAAAAA  GGTATTTAGA  GACAGAGAGA  GAAAAAGGCT  GAAATGGGTT    180

CGCTGGGTTC  TAAAAATCCG  CAAACCAAAC  AAGCCCAAGT  TCTTCTTTTG  GGACTTGACT    240

CAGCTGGGAA  GTCTACTCTC  CTTTATAAAT  TAAAGCTTGC  TAAGGATATT  ACCACCATCC    300

CTACAATAGG  TTTCAATGTG  GAAATGATCG  AGTTGGAAAG  GAATCTTTCA  CTCACAGTCT    360

GGGATGTTGG  AGGACAGGAA  AAAATGAGAA  CTGTTTGGGG  CTGTTACTGT  GAGAACACCG    420

ATGGGCTGGT  GTATGTTGTG  GACAGTACAG  ACAAACAGCG  ACTGGAAGAG  TCTCAGAGAC    480

AGTTTGAGCA  CATTTTGAAG  AATGAACACA  TTAAAAATGT  GCCTGTTGTT  CTATTAGCCA    540

ACAAACAAGA  CATGCCTGGA  GCTCTGACTG  CTGAGGACAT  CACCAGAATG  TTCAAAGTGA    600

AGAAGCTTTG  CAGTGACCGG  AACTGGTATG  TGCAACCCTG  CTGTGCCCTC  ACAGGGGAGG    660

GGCTGGCCCA  GGGGTTCAGG  AAATTAACTG  GATTTGTGAA  GAGCCACATG  AAATCAAGAG    720

GAGACACTTT  GGCGTTCTTC  AAGCAGAACT  GAGGCTGCGA  AAAATCCAAG  TCTCTACAGA    780

GACACTGATG  AAGTTGAAAG  GGTATTTGTT  TTTCCATGCC  CAATGAGGAA  ATCAAATTAA    840

TGAGTTGACA  AACTTTTCCT  GAGATGTAAT  TTCATCTACA  TTTAGGTAAA  ACACCTAAGA    900

ATGGTATCCA  AGAAAATAAT  TTAATTTTCA  AGCAAGGGAA  CTTTAGGCCA  ACCTTGTGGC    960

CATTGATCCA  CCGGGGAATT  GAAAACGGTA  TAATGGTTCT  CACAT                   1005

(2) INFORMATION FOR SEQ ID NO:    5:

(i) SEQUENCE CHARACTERISTICS:
          (A) LENGTH: 281 base pairs
          (B) TYPE: nucleic acid
          (C) STRANDEDNESS: single
          (D) TOPOLOGY: linear (vii) IMMEDIATE SOURCE:
          (A) LIBRARY: KERANOT02
          (B) CLONE: 823143H1
```

(xi) SEQUENCE DESCRIPTION: SEQ ID NO: 5 :

```
CGNTAACGTC GTGTCGNCCA CAGGTTTTAG TATTAAAGCA GTGCCATTCC AGANTGCCAT      60
CTTGANTGTA AAAGAACTTG GAGGGGNTGA TAACATCCGG AAATACTGGA GCCGNTACTA     120
CCAAGGATCT CAAGGGGTAA TATTTGTATT AGACAGTGCC TNTTCAGAGG NTGATTTAGA     180
AGCTGCTAGA AATGAGCTGC ACTCAGNTNT TCAGCATCCA CAGTTATGCA CTTTACCCTT     240
TTTAATATTG GCCAATCATC AAGACAAGCC AGCAGCTCGC T                         281
```

(2) INFORMATION FOR SEQ ID NO: 6:

(i) SEQUENCE CHARACTERISTICS:
        (A) LENGTH: 664 base pairs
        (B) TYPE: nucleic acid
        (C) STRANDEDNESS: single
        (D) TOPOLOGY: linear (vii) IMMEDIATE SOURCE:
        (A) LIBRARY: KERANOT02
        (B) CLONE: 823143R6

(xi) SEQUENCE DESCRIPTION: SEQ ID NO: 6 :

```
CCGATAACGT CGTGTCGACC ACAGGTTTTA GTATTAAAGC AGTGCCATTC CAGAATGCCA      60
TCTTGAATGT AAAAGAACTT GGAGGGGCTG ATAACATCCG GAAATACTGG AGCCGCTACT     120
ACCAAGGATC TCAAGGGGTA ATATTTGTAT TAGACAGTGC CTCTTCAGAG GATGATTTAG     180
AAGCTGCTAG AAATGAGCTG CACTCAGCTC TTCAGCATCC ACAGTTATGC ACTTTACCCT     240
TTTTAATATT GGCCAATCAT AAGACAAGCC AGCAGCTCGC TCAGTACAAG AGATNAAAAA     300
ATATTTTGAA CTTGAACCAC TTGCNCGTGG AAAACGCTGG ATTCTACAGC CCTGCTCACT     360
GGATGACCTG GATGGCNCTG NAAGACCAGN TCTCTCAGNN GANTNNNTTG TTAGAAGAAA     420
AAGACCATGA AGCTGTAAGN ATGGTGAAAT TCTGGGCAAA GAAAACAGGG CTCCCCNAAA     480
GGGCCTTGAA ACCTATCATG TTAGTTTCCT CATTTTAATN TTAATTTTGG GNAATCCAGA     540
CTATATTGGG GCTTCCGGAA TCCAANTTTT CCNCCTGGNG CATTTTCCAG ACTTNTCCAT     600
CTTCTCCCAA TTTAAANGGG AATNATTCCT GGTNGGATTC CGGATGGAAT TTATCCTGNG     660
GNGC                                                                  664
```

(2) INFORMATION FOR SEQ ID NO: 7:

(i) SEQUENCE CHARACTERISTICS:
        (A) LENGTH: 235 base pairs
        (B) TYPE: nucleic acid
        (C) STRANDEDNESS: single
        (D) TOPOLOGY: linear (vii) IMMEDIATE SOURCE:
        (A) LIBRARY: 293TF2T01
        (B) CLONE: 3464110H1

(xi) SEQUENCE DESCRIPTION: SEQ ID NO: 7 :

```
CTTTTTCAGG NGCTGCTCGC TCNCAGCCAG AGACGCTGCT TTTTTTTTCC GGGTTCGGAG      60
CCGTTCCGGA TGCTTTAGGC TGCCGGATGT CTGATCTCCG GATAACTGAG GCGTTTCTGT     120
ACATGGATTA TCTGTGTTTT AGAGCACTTT GCTGCAAGGG ACCACCACCT GCACGACCAG     180
AATATGACCT GGTTTGCATA GGCCTCACAG GTTCTGGCAA AACCAGTCTG TTGTC          235
```

(2) INFORMATION FOR SEQ ID NO: 8:

(i) SEQUENCE CHARACTERISTICS:
        (A) LENGTH: 245 base pairs

```
        (B) TYPE: nucleic acid
        (C) STRANDEDNESS: single
        (D) TOPOLOGY: linear (vii) IMMEDIATE SOURCE:
        (A) LIBRARY: ESOGNOT04
        (B) CLONE: 3384609H1

(xi) SEQUENCE DESCRIPTION: SEQ ID NO: 8 :

GTGCGGACCG TTCCGGATGC TTTAGGCTGC CGGATGTCTG ATCTCCGGAT AACTGAGGCG      60

TTTCTGTACA TGGATTATCT GTGTTTTAGA GCACTTTGCT GCAAGGGACC ACCACCTGCA     120

CGACCAGAAT ATGACCTGGT TTGCATAGGC CTCACAGGTT CTGGCAAAAC CAGTCTGTTG     180

TCCAAACTCT GCAGTGAAAG CCCCGATAAC GTCGTGTCGA CCACAGGTTT TAGTATTAAA     240

GCAGT                                                                245

(2) INFORMATION FOR SEQ ID NO:    9:

(i) SEQUENCE CHARACTERISTICS:
        (A) LENGTH: 175 base pairs
        (B) TYPE: nucleic acid
        (C) STRANDEDNESS: single
        (D) TOPOLOGY: linear (vii) IMMEDIATE SOURCE:
        (A) LIBRARY: COLNNOT13
        (B) CLONE: 1333754H1

(xi) SEQUENCE DESCRIPTION: SEQ ID NO: 9 :

AGGTATTTAG AGACAGAGAG AGAAAAAGGC TGAAATGGGT TCGCTGGGTT CTAAAAATCC      60

GCAAACCAAA CAAGCCCAAG TTCTTCTTTT GGGACTTGAC TCAGCTGGGA AGTCTACTCT     120

CCTTTATAAA TTAAAGCTTG CTAAGGATAT TACCACCATC CCTACAATAG GTTTC         175

(2) INFORMATION FOR SEQ ID NO:    10:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (vii) IMMEDIATE SOURCE:
        (A) LIBRARY: COLNNOT27
        (B) CLONE: 1802032H1

(xi) SEQUENCE DESCRIPTION: SEQ ID NO: 10 :

GTGAGAACAC CGATGGGCTG GTGTATGTTG TGGACAGTAC AGACAAACAG CGACTGGAAG      60

AGTCTCAGAG ACAGTTTGAG CACATTTTGA AGAATGAACA CATTAAAAAT GNGCCTGNTG     120

TTCTATTAGC CANCAAACAA GACATGCCTG GAGCTCTGAC TGCTGAGGAC ATCACCNGAA     180

TGTTCAAAGT GAAGAAGCTT TGCAGTGA                                       208

(2) INFORMATION FOR SEQ ID NO:    11:

(i) SEQUENCE CHARACTERISTICS:
        (A) LENGTH: 572 base pairs
        (B) TYPE: nucleic acid
        (C) STRANDEDNESS: single
        (D) TOPOLOGY: linear (vii) IMMEDIATE SOURCE:
        (A) LIBRARY: COLNNOT27
        (B) CLONE: 1802320F6

(xi) SEQUENCE DESCRIPTION: SEQ ID NO: 11 :
```

```
GGAAGAGTCT CAGAGACAGT TTGAGCACAT TTTGAAGAAT GAACACATTA AAAATGTGCC      60

TGTTGTTCTA TTAGCCAACA AACAAGACAT GCCTGGAGCT CTGACTGCTG AGGACATCAC     120

CAGAATGTTC AAAGTGAAGA AGCTTTGCAG TGACCGGAAC TGGTATGTGC AACCCTGCTG     180

TGCCCTCACA GGGGAGGGGC TGGCCCAGGG GTTCAGGAAA TTAACTGGAT TTGTGAAGAG     240

CCACATGAAA TCAAGAGGAG ACACTTTGGC GTTCTTCAAG CAGAACTGAG GCTGCGAAAA     300

AATCCAAGTC TCTACAGANG ACACTGATGA AGTTGAAAGG GTAATTGTTT TTCCCATGCC     360

AAATGAGGGA AANCCAAATT AATGAGTTGA CAAAACTTTT CCTGAGATGG TAATTTCCAT     420

CCTACATTTT AGTTAAAACA ACCTTAAGAA TGNANATCCA AGGAAAATAA NTTAAATTTT     480

CAAGNCCANG GAACCTTTTA NGCAAAACCT GNGGGCCAAN TGGATCCACT NGGGGAAATG     540

GAAAAACCGG TNNTAAAAGG NTNCTAACAA AT                                   572

(2) INFORMATION FOR SEQ ID NO:     12:

(i) SEQUENCE CHARACTERISTICS:
         (A) LENGTH: 448 base pairs
         (B) TYPE: nucleic acid
         (C) STRANDEDNESS: single
         (D) TOPOLOGY: linear (vii) IMMEDIATE SOURCE:
         (A) LIBRARY: ISLTNOT01
         (B) CLONE: 2073315F6

(xi) SEQUENCE DESCRIPTION: SEQ ID NO: 12 :

GAGAGAAAAA GGCTGAAATG GGTTCGCTGG GTTCTAAAAA TCCGCAAACC AAACAAGCCC      60

AAGTTCTTCT TTTGGGACTT GACTCAGCTG GGAAGTCTAC TCTCCTTTAT AAATTAAAGC     120

TTGCTAAGGA TATTACCACC ATCCCTACAA TAGGTTTCAA TGTGGAAATG ATCGAGTTGG     180

AAAGGAATCT TTCACTCACA GTCTGGGATG TTGGAGGACA GGAAAAAATG AGAACTGTTT     240

GGGGCTGTTA CTGTGAGAAC ACCGATGGGC TGGTGTATGT TGTGGACAGT ACAGACAAAC     300

AGCGACTGGA AGAGTCTCAG AGACAGTTTG AGCACATTTT GAAGAATGAC CACATTAAAA     360

ATGTGCCTGT TGTCTATTAG CCAACCAAAC AAGACATGCC TGGAGCTNTG ACTGCTGAGG     420

ACATCACCAG AATGTTCAAA GTGAAGAA                                        448

(2) INFORMATION FOR SEQ ID NO:     13:

(i) SEQUENCE CHARACTERISTICS:
         (A) LENGTH: 259 base pairs
         (B) TYPE: nucleic acid
         (C) STRANDEDNESS: single
         (D) TOPOLOGY: linear (vii) IMMEDIATE SOURCE:
         (A) LIBRARY: GBLANOT01
         (B) CLONE: 2614213H1

(xi) SEQUENCE DESCRIPTION: SEQ ID NO: 13 :

ATAAACACAT CTAGGTTCTT GTTCTTAGAA TACAGCATGA AGAATTTGCT TTCTTCTTTC      60

TTCCTAACAT TTTCATGTGA GATCCAGAAA GGACACATTG TCTCTGGCCA TTCGnnnnnn     120
nnnnnnnnnn nnnnnnnnnn GGTATTTAGA GACAGAGAGA GAAAAAGGCT GAAATGGGTT     180

CGCTGGGTTC TAAAAATCCG CAAACCAAAC AAGCCCAAGT TCTTCTTTTG GGACTTGACT     240

CAGCTGGGAA GTCTACTCT                                                  259

(2) INFORMATION FOR SEQ ID NO:     14:
```

-continued

```
    (i) SEQUENCE CHARACTERISTICS:
         (A) LENGTH: 175 amino acids
         (B) TYPE: amino acid
         (C) STRANDEDNESS: single
         (D) TOPOLOGY: linear (vii) IMMEDIATE SOURCE:
         (A) LIBRARY: GenBank
         (B) CLONE: g178989

(xi) SEQUENCE DESCRIPTION: SEQ ID NO: 14 :

Met Gly Lys Val Leu Ser Lys Ile Phe Gly Asn Lys Glu Met Arg
                 5                  10                  15

Ile Leu Met Leu Gly Leu Asp Ala Ala Gly Lys Thr Thr Ile Leu
                20                  25                  30

Tyr Lys Leu Lys Leu Gly Gln Ser Val Thr Thr Ile Pro Thr Val
                35                  40                  45

Gly Phe Asn Val Glu Thr Val Thr Tyr Lys Asn Val Lys Phe Asn
                50                  55                  60

Val Trp Asp Val Gly Gly Gln Asp Lys Ile Arg Pro Leu Trp Arg
                65                  70                  75

His Tyr Tyr Thr Gly Thr Gln Gly Leu Ile Phe Val Val Asp Cys
                80                  85                  90

Ala Asp Arg Asp Arg Ile Asp Glu Ala Arg Gln Glu Leu His Arg
                95                 100                 105

Ile Ile Asn Asp Arg Glu Met Arg Asp Ala Ile Ile Leu Ile Phe
               110                 115                 120

Ala Asn Lys Gln Asp Leu Pro Asp Ala Met Lys Pro His Glu Ile
               125                 130                 135

Gln Glu Lys Leu Gly Leu Thr Arg Ile Arg Asp Arg Asn Trp Tyr
               140                 145                 150

Val Gln Pro Ser Cys Ala Thr Ser Gly Asp Gly Leu Tyr Glu Gly
               155                 160                 165

Leu Thr Trp Leu Thr Ser Asn Tyr Lys Ser
               170                 175
```